United States Patent [19]

Suzuki et al.

[11] Patent Number: 5,525,607

[45] Date of Patent: Jun. 11, 1996

[54] XANTHINE COMPOUNDS

[75] Inventors: Fumio Suzuki, Mishima; Junichi Shimada, Shizuoka-ken; Akio Ishii, Shizuoka-ken; Tetsuji Ohno, Shizuoka-ken; Akira Karasawa, Shizuoka-ken; Kazuhiro Kubo, Shizuoka-ken; Hiromi Nonaka, Shizuoka-ken; Fumio Suzuki, Mishima; Junichi Shimada, Shizuoka-ken; Akio Ishii, Shizuoka-ken; Tetsuji Ohno, Shizuoka-ken, all of Japan; Akira Karasawa, Huntingdon Valley, Pa.; Kazuhiro Kubo; Hiromi Nonaka, both of Shizuoka-ken, Japan

[73] Assignee: Kyowa Hakko Kogyo Co., Ltd, Tokyo, Japan

[21] Appl. No.: 63,684

[22] Filed: May 20, 1993

Related U.S. Application Data

[60] Division of Ser. No. 839,690, Feb. 24, 1992, Pat. No. 5,290,782, which is a continuation-in-part of Ser. No. 574,447, Aug. 29, 1990, abandoned.

[30] Foreign Application Priority Data

| Sep. 1, 1989 | [JP] | Japan | 1-226642 |
| Feb. 25, 1991 | [JP] | Japan | 3-029796 |

[51] Int. Cl.⁶ .................... A61K 31/52; C07D 473/00
[52] U.S. Cl. .................... 514/263; 544/267
[58] Field of Search .................... 544/267; 514/263

[56] References Cited

U.S. PATENT DOCUMENTS

| 4,548,820 | 10/1985 | Regnier et al. | 514/255 |
| 4,603,203 | 7/1986 | Furukawa et al. | 544/262 |
| 4,925,847 | 5/1990 | Hofer | 544/273 X |

FOREIGN PATENT DOCUMENTS

| 0256692 | 7/1987 | European Pat. Off. . |
| 0267607 | 5/1988 | European Pat. Off. . |
| 0374808 | 6/1990 | European Pat. Off. . |
| 0415456 | 3/1991 | European Pat. Off. . |
| 0031772 | 11/1964 | Germany . |
| 1245969 | 8/1967 | Germany . |
| 4019892 | 1/1992 | Germany . |
| 1201997 | 8/1970 | United Kingdom . |
| 0000297 | 4/1992 | WIPO . |

OTHER PUBLICATIONS

CA103:129078, Sunshine, "Analgesic and Antiinflammatory . . . ", WO 8502542, Dec. 12, 1984.
Chem. Abs., vol. 63, No. 13 (Dec. 20, 1965) 18120d.
Mol. Pharm., vol. 31 (1987) 247.
Biochem. Pharm., vol. 37 (1988) 3653.
Br. J. Pharm., vol. 96 (1989) 31P.
Br. J. Pharm., vol. 97 (1989) 502P.
J. Pharm. Exp. Ther., vol. 248, No. 2 (1989) 589.
Phys. & Pharm. (1988) 39.
J. Med. Chem., vol. 14 (1971) 1202.
J. Med. Chem., vol. 31 (1988) 613.
J. Med. Chem., vol. 32 (1989) 1231.
J. Med. Chem., vol. 32 (1989) 1873.
J. Med. Chem., vol. 33 (1990) 1906.
Tetrahedron Lett., vol. 27 (1986) 6337.
Merck Index, 10th Ed. (1983) 9110.

*Primary Examiner*—Gary Geist
*Assistant Examiner*—Catherine Kilby Scalzo
*Attorney, Agent, or Firm*—Fitzpatrick, Cella, Harper & Scinto

[57] ABSTRACT

Novel xanthine compounds represented by the following formula:

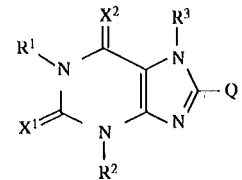

wherein each of $R^1$, $R^2$ and $R^3$ independently represents hydrogen or lower alkyl;
each of $X^1$ and $X^2$ independently represents oxygen or sulfur; and Q represents:

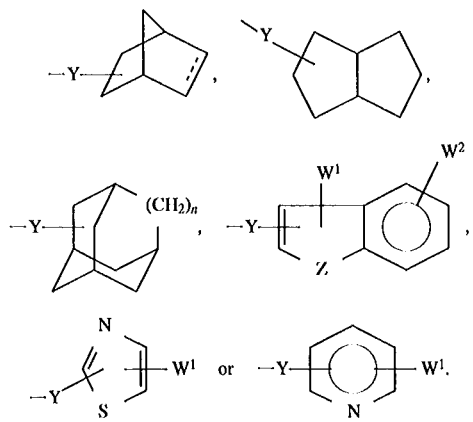

The compounds are useful as a diuretic, a renal-protecting agent and bronchodilator.

5 Claims, No Drawings

XANTHINE COMPOUNDS

This application is a division of application Ser. No. 839,690, now U.S. Pat. No. 5,290,782 filed Feb. 24, 1992, which is a continuation-in-part of application Ser. No. 574,447, filed Aug. 29, 1990, now abandoned.

BACKGROUND OF THE INVENTION

The present invention relates to novel xanthine compounds having a diuretic effect, a renal-protecting effect and a bronchodilatory effect.

Heretofore, theophylline, i.e., 1,3-dimethylxanthine has been known as a diuretic, a vasodilator, etc. [The Merck Index, 10th edition, 9110 (1983)].

Xanthine compounds carrying, at the 8-position thereof, substituents such as alkyl, alicyclic alkyl, aralkyl, aryl, etc. have a diuretic effect, as disclosed in East German Patent No. 31,772 [Chem. Abst., 63, 18120d (1965)] and West German Patent No. 1,245,969 [Chem. Abst., 67, 90994n (1967)].

In relation to the compounds of the present invention, 8-(1-adamantyl)-1,3,7-trimethylxanthine is described in Tetrahedron Lett., 27, 6337 (1986). However, nothing is mentioned on its pharmacological effect.

The object of the present invention is to provide novel xanthine compounds exhibiting strong diuretic and renal-protecting effect, based on the finding that xanthine compounds which are adenosine receptor antagonists, particularly those having an activity of selectively antagonizing adenosine $A_1$ receptor, have strong diuretic and renal-protecting effect.

SUMMARY OF THE INVENTION

The present invention relates to a xanthine compound represented by the following formula (I):

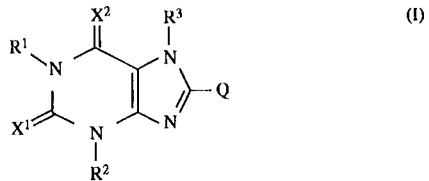

wherein each of $R^1$, $R^2$ and $R^3$ independently represents hydrogen or lower alkyl;
each of $X^1$ and $X^2$ independently represents oxygen or sulfur; and Q represents:

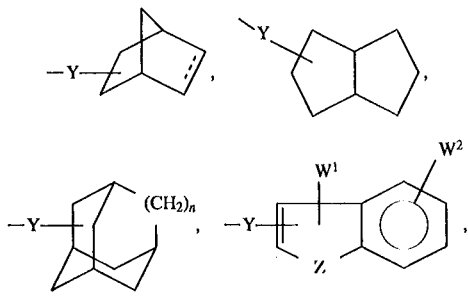

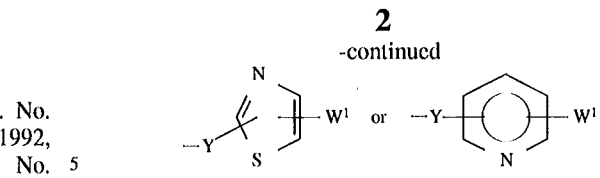

where ----- represents a single bond or a double bond; Y represents a single bond or alkylene, n represents 0 or 1, each of $W^1$ and $W^2$ independently represents hydrogen, lower alkyl or amino, Z represents $-CH_2-$, $-O-$, $-S-$ or $-NH-$;
provided that when Q is

then $R^1$, $R^2$ and $R^3$ are not simultaneously methyl; [hereinafter referred to as "Compound (I)" and compounds with other formula numbers are likewise referred to], or a pharmaceutically acceptable salt thereof.

DETAILED DESCRIPTION OF THE INVENTION

In the definition of the respective groups in the formula (I), the lower alkyl includes straight or branched alkyl having 1 to 6 carbon atoms, for example, methyl, ethyl, propyl, isopropyl, butyl, isobutyl, sec-butyl, tert-butyl, pentyl, neopentyl, hexyl, etc. The alkylene includes straight or branched alkylene having 1 to 4 carbon atoms, for example, methylene, ethylene, trimethylene, tetramethylene, methylmethylene, propyplene, ethylethylene, etc.

The pharmaceutically acceptable salt of Compound (I) includes pharmaceutically acceptable acid addition salt, metal salt, ammonium salt, organic amine addition salt, amino acid addition salt, etc.

The pharmaceutically acceptable acid addition salt of Compound (I) includes inorganic acid salt such as hydrochloride, sulfate, phosphate, etc., and organic acid salt such as acetate, maleate, fumarate, oxalate, citrate, etc.

The pharmaceutically acceptable metal salt includes alkali metal salt such as sodium salt, potassium salt, etc., alkaline earth metal salt such as magnesium salt, calcium salt, etc., and also aluminum and zinc salts.

The pharmaceutically acceptable ammonium salt includes salts of ammonium, tetramethylammonium, etc. The pharmaceutically acceptable organic amine addition salt includes addition salts of morpholine, piperidine, etc., and the pharmaceutically acceptable amino acid addition salt includes addition salts of lysine, glycine, phenylalanine, etc.

A process for producing Compound (I) of the present invention is described below.

Compound (I-1) which is Compound (I) wherein $R^3$ is hydrogen, is produced by the following production steps:

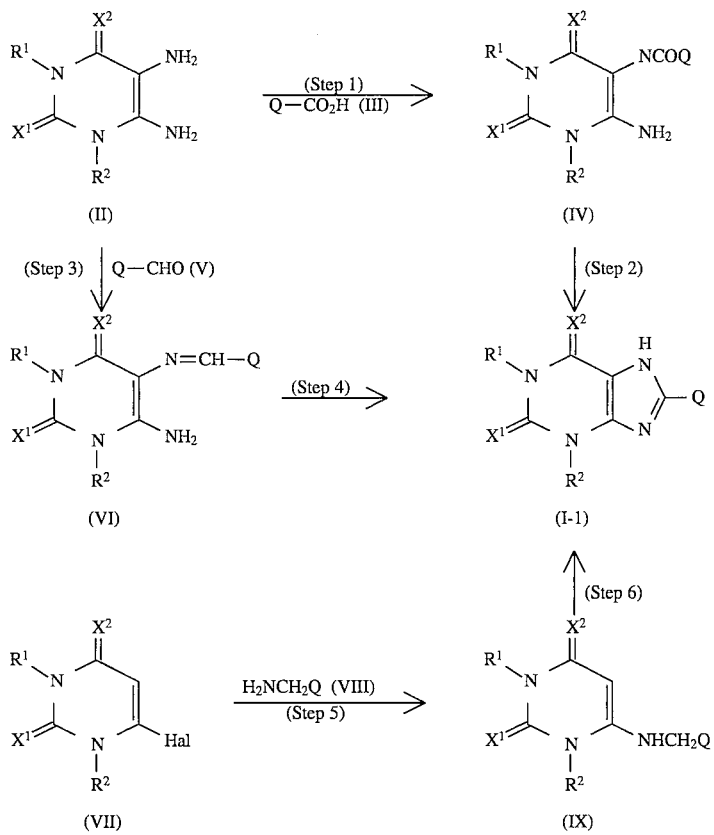

wherein Hal represents halogen such as chlorine, bromine or iodine and $R^1$, $R^2$, $X^1$, $X^2$ and Q have the same meanings as defined above.

Step 1:

A Compound (IV) can be obtained by reacting a uracil derivative (II) obtained according to a well known process [for example, the process disclosed in Japanese Published Unexamined Patent Application No. 42383/84] with carboxylic acid (III) or a carboxylic acid reactive derivative.

The carboxylic acid reactive derivative includes acid halides such as acid chlorides, acid bromides, etc., active esters such as p-nitrophenyl ester, N-oxysuccinimide ester, etc., acid anhydrides commercially available or those formed from carbodiimides such as 1-ethyl-3-(3-dimethylaminopropyl)carbodiimide, diisopropylcarbodiimide, dicyclohexylcarbodiimide, etc.; mixed acid anhydrides with monoethyl carbonate, monoisobutyl carbonate, etc. and so forth.

The reaction of Compound (II) with Compound (III) is carried out without any solvent at a temperature of 50° to 200° C. In the case of using the carboxylic acid reactive derivative, the reaction can be carried out according to a process usually used in the peptide chemistry. For example, the reaction solvent is properly selected from halogenohydrocarbons such as methylene chloride, chloroform, dichloroethane, etc., ethers such as dioxane, tetrahydrofuran, etc., dimethylformamide and dimethylsulfoxide, and if necessary water is used. The reaction temperature is −80° to 50° C., and the reaction is completed for 0.5 to 24 hours. Sometimes, the reaction may be favorably carried out, if necessary, in the presence of an additive such as 1-hydroxybenzotriazole, etc., or a base such as pyridine, triethylamine, dimethylaminopyridine, N-methylmorpholine, etc. Furthermore, the carboxylic acid reactive derivative may be formed in the reaction system and used without isolation.

Step 2:

A desired Compound (I-1) is obtained from Compound (IV) by the reaction in the presence of a base (process A), by treatment with a dehydrating agent (process B), or by heating (process C).

As the preferable base in the process A, alkali metal hydroxides such as sodium hydroxide, potassium hydroxide, etc. can be exemplified. As the reaction solvent, water, lower alcohols such as methanol, ethanol, etc., ethers such as dioxane, tetrahydrofuran, etc., dimethylformamide, dimethylsulfoxide, etc. can be used alone or in combination. The reaction is carried out at a temperature of from room temperature to 180° C. and is usually completed for 10 minutes to 6 hours.

As the dehydrating agent for use in the process B, thionyl halides such as thionyl chloride, etc., and phosphorus oxyhalides such as phosphorus oxychloride, etc. can be used, and the reaction is carried out at a temperature of from room temperature to 180° C. without any solvent or in a solvent inert to the reaction, for example, halogenohydrocarbons such as methylene chloride, chloroform, dichloroethane, etc., dimethylformamide, dimethylsulfoxide, etc. and is usually completed for 0.5 to 12 hours.

In the case of process C, the Compound (I-1) can be obtained by heating Compound (IV) at a temperature of 50° to 200° C. in a polar solvent such as dimethylsulfoxide, dimethylformamide, Dowthermo A (product of Muromachi Kagaku Kogyo Kaisha, Ltd.), etc.

Step 3:

A schiff base (VI) can be obtained by reacting Compound (II) with aldehyde (V) in a mixed solvent such as a mixture of acetic acid with a lower alcohol such as methanol, ethanol, etc. at a temperature of −20° to 100° C.

Step 4:

A desired Compound (I-1) can be obtained by subjecting Compound (VI) to an oxidative cyclization reaction.

As the appropriate oxidizing agent, oxygen, ferric chloride, cerium$^{IV}$ ammonium nitrate, diethyl azodicarboxylate, etc. can be exemplified. The reaction is carried out by heating Compound (VI) at from room temperature to 180° C. in the presence of the afore-mentioned oxidizing agent and, if necessary, in a solvent inert to the reaction, for example, a lower alcohol such as methanol, ethanol, etc., a halogenohydrocarbon such as methylene chloride, chloroform, etc., or an aromatic hydrocarbon such as toluene, xylene, nitrobenzene, etc.

Step 5:

A Compound (IX) can be obtained by reacting a uracil derivative (VII) obtained according to a well known process, for example, the process described in Japanese Published Unexamined Patent Application No. 5082/86 with an amine (VIII) in a solvent inert to the reaction, for example, a lower alcohol such as methanol, ethanol, etc., dimethylformamide, dimethylsulfoxide, etc. alone or in combination thereof at a temperature of 50° to 150° C.

Step 6:

A Compound (I-1) can be obtained by reacting a Compound (IX) with a nitrosating agent such as sodium nitrite, isoamyl nitrite, etc. under an acidic condition with dilute hydrochloric acid, etc. in a solvent inert to the reaction, for example, a lower alcohol such as methanol, ethanol, etc. usually at a temperature of from room temperature to the boiling point of the solvent.

Step 7:

A Compound (I-2) which is Compound (I) wherein R$^3$ is a lower alkyl group can be obtained through the following step:

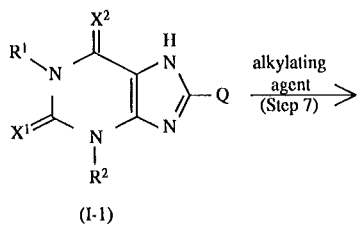

(I-1)

alkylating agent (Step 7) →

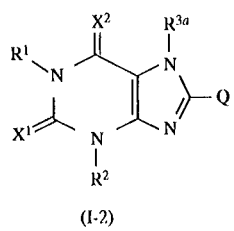

(I-2)

wherein R$^1$, R$^2$, X$^1$, X$^2$ and Q have the same meanings as defined above, R$^{3a}$ represents lower alkyl in the definition of R$^3$.

A desired compound (I-2) can be obtained by reacting Compound (I-1) obtained in Steps 1 to 6 with an alkylating agent preferably in the presence of a base.

As the alkylating agent, alkyl halides, dialkyl sulfates, diazoalkanes, etc. are used.

As the base, an alkali metal carbonate such as sodium carbonate, potassium carbonate, etc., an alkali metal hydride such as sodium hydride, etc., and an alkali metal alkoxide such as sodium methoxide, sodium ethoxide, etc. are exemplified. The reaction is completed at a temperature of 0° to 180° C. usually for 0.5 to 24 hours.

Step 8:

Compound (I-4) which is Compound (I) wherein X$^2$ is sulfur, can be obtained by the following step.

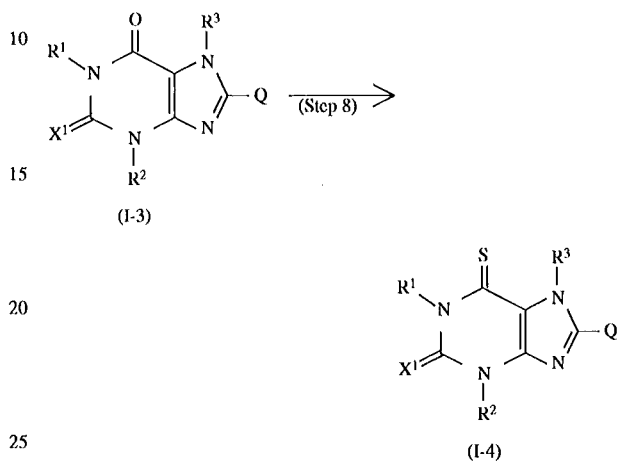

wherein R$^1$, R$^2$, R$^3$, X$^1$ and Q have the same meanings as previously defined.

A desired Compound (I-4) was prepared by reacting Compound (I-3) which is Compound (I) wherein X$^2$ is oxygen, with an appropriate thionation reagent, in an inert solvent. As the thionation reagent, phosphorus pentasulfide and the like are mentioned. As the solvent, dimethylformamide, tetrahydrofuran, dioxane, etc. are mentioned, and preferably pyridine and the like are used. The reaction is carried out at a temperature of 50° to 180° C. for a period of 10 minutes to 36 hours.

The intermediates and the desired compound obtained according to the aforementioned processes can be isolated and purified by subjecting them to a purification process usually used in the organic synthetic chemistry, for example, filtration, extraction, washing, drying, concentration, recrystallization, various chromatographics, etc. The intermediates can be used in the successive reaction without any purification.

Salts of Compound (I) can be obtained by direct purification when Compound (I) can be obtained in a salt form, or by formation of a salt according to a usual procedure when the Compound (I) is obtained in a free form, and a subsequent purification.

Compound (I) and its pharmaceutically acceptable salts sometimes exist in an adduct form with water or various other solvents, and these adducts are included in the present invention.

Optical isomers may exist with respect to Compound (I), and all the possible stereoisomers and their mixtures are also included in the scope of the present invention.

Specific examples of Compound (I) are shown in Table 1.

TABLE 1
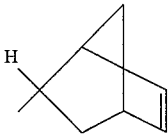
| Compound No. (Example No.) | R¹ | R² | R³ | Q | X¹ | X² |
|---|---|---|---|---|---|---|
| 1 (1) | n-C$_3$H$_7$ | n-C$_3$H$_7$ | H |  | O | O |
| 2 (1) | n-C$_3$H$_7$ | n-C$_3$H$_7$ | H | 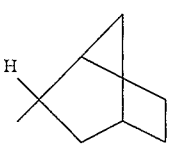 | O | O |
| 3 (2) | n-C$_3$H$_7$ | n-C$_3$H$_7$ | H | 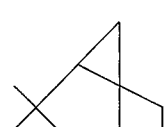 | O | O |
| 4 (2) | n-C$_3$H$_7$ | n-C$_3$H$_7$ | H | 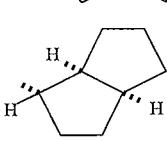 | O | O |
| 5 (3) | n-C$_3$H$_7$ | n-C$_3$H$_7$ | H | 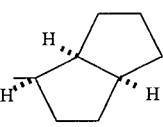 | O | O |
| 6 (3) | n-C$_3$H$_7$ | n-C$_3$H$_7$ | H | 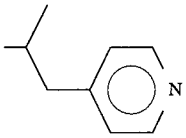 | O | O |
| 7 (4) | n-C$_3$H$_7$ | n-C$_3$H$_7$ | H | 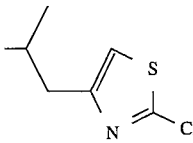 | O | O |
| 8 (5) | n-C$_3$H$_7$ | n-C$_3$H$_7$ | H | 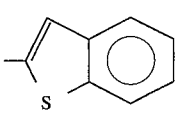 | O | O |
| 9 (6) | n-C$_3$H$_7$ | n-C$_3$H$_7$ | H | 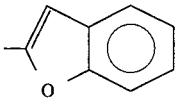 | O | O |
| 10 (7) | n-C$_3$H$_7$ | n-C$_3$H$_7$ | H |  | O | O |

TABLE 1-continued

| Compound No. (Example No.) | R¹ | R² | R³ | Q | X¹ | X² |
|---|---|---|---|---|---|---|
| 11 (8) | n-C$_3$H$_7$ | n-C$_3$H$_7$ | H | (methylindene) | O | O |
| 12 (9) | n-C$_3$H$_7$ | n-C$_3$H$_7$ | H | (4-ethyl-2-aminothiazole) | O | O |
| 13 (29) | n-C$_3$H$_7$ | n-C$_3$H$_7$ | H | (tricyclic alkyl) | O | O |
| 14 (10) | n-C$_3$H$_7$ | n-C$_3$H$_7$ | H | (tricyclic alkyl) | O | O |
| 15 (11) | n-C$_3$H$_7$ | n-C$_3$H$_7$ | H | (ethyl-tricyclic alkyl) | O | O |
| 16 (12) | n-C$_3$H$_7$ | n-C$_3$H$_7$ | H | (ethyl-bicyclic alkyl) | O | O |
| 17 (13) | n-C$_3$H$_7$ | n-C$_3$H$_7$ | CH$_3$ | (norbornenyl) | O | O |
| 18 (14) | n-C$_3$H$_7$ | n-C$_3$H$_7$ | CH$_3$ | (bicyclic alkyl) | O | O |
| 19 (30) | n-C$_3$H$_7$ | n-C$_3$H$_7$ | CH$_3$ | (tricyclic alkyl) | O | O |

TABLE 1-continued

| Compound No. (Example No.) | R¹ | R² | R³ | Q | X¹ | X² |
|---|---|---|---|---|---|---|
| 20 (15) | n-$C_3H_7$ | n-$C_3H_7$ | $CH_3$ | (tetracyclic) | O | O |
| 21 (16) | n-$C_3H_7$ | n-$C_3H_7$ | $C_2H_5$ | (tetracyclic) | O | O |
| 22 (17) | n-$C_3H_7$ | n-$C_3H_7$ | n-$C_3H_7$ | (tetracyclic) | O | O |
| 23 (18) | H | n-$C_3H_7$ | H | (bicyclic with H stereochem.) | O | O |
| 24 (19) | n-$C_3H_7$ | n-$C_3H_7$ | H | (bicyclic with H stereochem.) | S | O |
| 25 (20) | H | n-$C_3H_7$ | H | (tetracyclic) | O | O |
| 26 (21) | H | n-$C_3H_7$ | H | (tetracyclic) | O | S |
| 27 (22) | $CH_3$ | $CH_3$ | H | (tetracyclic) | O | O |

TABLE 1-continued

| Compound No. (Example No.) | R¹ | R² | R³ | Q | X¹ | X² |
|---|---|---|---|---|---|---|
| 28 (23) | $C_2H_5$ | $C_2H_5$ | H | | O | O |
| 29 (24) | $n\text{-}C_4H_9$ | $n\text{-}C_4H_9$ | H | | O | O |
| 30 (25) | $CH_3$ | $iso\text{-}C_4H_9$ | H | | O | O |
| 31 (26) | $n\text{-}C_3H_7$ | $n\text{-}C_3H_7$ | H | | S | O |
| 32 (27) | $n\text{-}C_3H_7$ | $n\text{-}C_3H_7$ | H | | O | S |
| 33 (28) | $n\text{-}C_3H_7$ | $n\text{-}C_3H_7$ | H | | S | S |

Compound (I) and its pharmaceutically acceptable salts have an activity of selectively antagonizing adenosine $A_1$ receptor, and thus exhibit, a diuretic effect, a renal-protecting effect a bronchodilatory effect, etc. Compound (I) and its pharmaceutically acceptable salts are useful as a diuretic and renal-protecting agent, bronchodilatory agent, etc.

The pharmacological effects of Compound (I) are explained, referring to Test Examples.

Test Example 1, acute toxicity test

A test compound (300 mg/kg) was orally administered to male dd-strain mice having a body weight of 20±1 g (3 animals/group). Minimum lethal dose (MLD) of the compounds was determined by observing whether or not the mice were alive after 7 days of the administration.

With respect to Compound Nos. 1–5, 7–11, 13–18, 20 23, 24 and 31–33, the MLD was more than 300 mg/kg, and with respect to Compound No. 12, that was 300 mg/kg. This shows the toxicity of Compound (I) is weak and can be administered safely over a wide range of dosage.

Test Example 2, adenosine receptor binding test

1) Adenosine $A_1$ Receptor Binding

This test was conducted according to the method of Bruns et al. [Proc. Natl. Acad. Sci., 77, 5547 (1980)] with some modification.

Cerebrum of a guinea pig was suspended into ice cooled 50 mM tris hydroxymethyl aminomethane hydrochloride (Tris HCl) buffer (pH=7.7), by using Polytron homogenizer (manufactured by Kinematica Co.). The suspension was centrifuged (50,000×g, 10 minutes), and the precipitate was resuspended by adding the same volume of 50 mM Tris HCl buffer. The suspension was centrifuged under the same conditions, and the precipitate obtained was suspended once again by adding 10 volumes of 50 mM Tris HCl. The tissue suspension was incubated at 37° C. for 30 minutes in the presence of 0.02 units/mg tissue of adenosine deaminase (manufactured by Sigma Co.). The resulting tissue suspension was recentrifuged (50,000×g, 10 minutes), and 50 mM Tris HCl was added to the Precipitate to adjust the concentration of tissue to 10 mg (wet weight)/ml.

To 1 ml of tissue suspension prepared above were added 50 μl of [$^3$H] cyclohexyladenosine [$^3$H-CHA, 27 Ci/mmol, manufactured by New England Nuclear Co.] (final concentration=1.1 nM) and 50 μl of test compound. The mixture was incubated at 25° C. for 90 minutes, and the resulting mixture was stopped by rapid vacuum filtration through a glass fiber filter (GF/C manufactured by Whatman Co.) and immediately washed three times with 5 ml each of ice cold 50 mM Tris HCl buffer. The filter was transferred to a vial bottle, and a scintillator (EX-H by Wako Pure Chemicals Industries, Ltd.) was added thereto. Its radioactivity was then determined by a scintillation counter (manufactured by Packard Instrument Co.).

The inhibition rate of the test compound against the binding of $A_1$ acceptor ($^3$H-CHA binding) was calculated from the following equation:

$$\text{Inhibition (\%)} = \left(1 - \frac{[B]-[N]}{[T]-[N]}\right) \times 100$$

[Notes]

1. "B" means the radioactivity of $^3$H-CHA bound in the presence of a test compound at a concentration shown in Table 2.
2. "T" means the radioactivity of $^3$H-CHA bound in the absence of test compounds.
3. "N" means the radioactivity of $^3$H-CHA bound in the presence of 10 μM of $N^6$-(L-2-phenylisopropyl)adenosine (manufactured by Sigma Co.).

The results are shown in Table 2. The inhibition constant (Ki value) shown in the table was calculated from Cheng-Prusoff's equation.

2) Adenosine $A_2$ Acceptor Binding Test

This test was conducted according to the method of Bruns et al. [Mol. Pharmacol., 29,331 (1986)] with some modification.

A precipitate was prepared from rat corpus striatum in a similar manner as in 1) above. The precipitate was suspended by adding a 50 mM Tris HCl buffer containing 10 mM magnesium chloride and 0.02 unit/mg (tissue) of adenosine deaminase (manufactured by Sigma Co.) to adjust the concentration of tissue to 5 mg (wet weight)/ml.

To 1 ml of tissue suspension prepared above were added 50 μl of a mixture of N-ethylcarboxamidoadenosine [$^3$H-NECA, 26 Ci/mmol, manufactured by Amersham Co.] (final concentration=3.8 nM) and cyclopentyladenosine [CPA, manufactured by Sigma Co.] (final concentration=50 nM), and 50 μl of test compound. The mixture was incubated at 25° C. for 120 minutes. The resulting mixture was treated in the same manner as in 1) above to determine its radioactivity.

The inhibition rate of the test compound against the binding of $A_2$ receptor ($^3$H-NECA binding) was calculated from the following equation:

$$\text{Inhibition Rate (\%)} = \left(1 - \frac{[B]-[N]}{[T]-[N]}\right) \times 100$$

[Notes]

1. "B" means the radioactivity of $^3$H-NECA bound in the presence of a test compound at a concentration shown in Table 2.
2. "T" means the radioactivity of $^3$H-NECA bound in the absence of test compounds.
3. "N" means the radioactivity of $^3$H-NECA bound in the presence of 100 μM of CPA.

The results are shown in Table 2. The Ki values shown in the table were calculated from the following equation:

$$Ki = \frac{IC_{50}}{1 + \frac{L}{Kd} + \frac{C}{Kc}}$$

[Notes]

$IC_{50}$: Concentration at an inhibition rate of 50%

L: Concentration of $^3$H-NECA

Kd: Dissociation constant of $^3$H-NECA

C: Concentration of CPA.

Kc: Inhibition constant of CPA

TABLE 2

| Compound No. | $A_1$ Receptor | | $A_2$ Receptor | | Ratio of Ki Values [$A_2/A_1$] |
|---|---|---|---|---|---|
| | Inhibition (%)/ Concentration of Tested Compound [$10^{-5}/10^{-4}$M] | Ki (nM) | Inhibition (%)/ Concentration of Tested Compound [$10^{-5}/10^{-4}$M] | Ki (nM) | |
| 1 | 99/99 | 5.5 | 88/97 | 510 | 92.7 |
| 3 | 100/100 | 4.4 | 83/90 | 330 | 75.0 |
| 5 | 99/99 | 3.8 | 91/99 | 330 | 86.8 |
| 6 | 100/101 | 5.0 | 70/85 | 560 | 112 |
| 13 | 100/100 | 7.8 | 63/71 | 1,400 | 179 |
| 14 | 101/101 | 1.3 | 63/77 | 380 | 292 |
| 28 | 100/101 | 7.1 | 61/78 | 940 | 132 |
| 29 | 100/100 | 9.1 | 72/78 | 970 | 107 |
| XAC*[1] | 98 ($10^{-6}$M) | 11 | 99/— | 21 | 1.91 |
| PD 115199*[2] | 97/100 | 190 | 94/98 | 26 | 0.14 |
| CGS 15943*[3] | 99/96 | 10 | 99/97 | 0.73 | 0.073 |

TABLE 2-continued

| Compound No. | $A_1$ Receptor Inhibition (%)/ Concentration of Tested Compound [$10^{-5}/10^{-4}$ M] | Ki (nM) | $A_2$ Receptor Inhibition (%)/ Concentration of Tested Compound [$10^{-5}/10^{-4}$ M] | Ki (nM) | Ratio of Ki Values [$A_2/A_1$] |
|---|---|---|---|---|---|
| Theophylline | 33/74 | 23,000 | 26/69 | 20,000 | 0.87 |

[Notes]
*1: Xanthineaminecongener

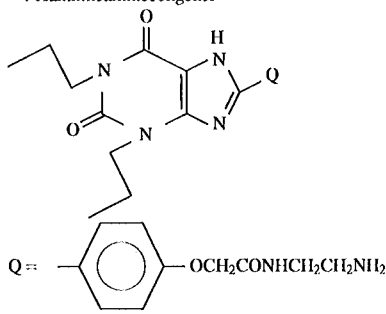

[Mol. Pharmacol., 29, 126 (1986)]

*2: 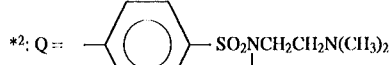

[Naunyn-Schmiedeberg's Arch. Pharmacol., 335, 64 1987)]

*3: 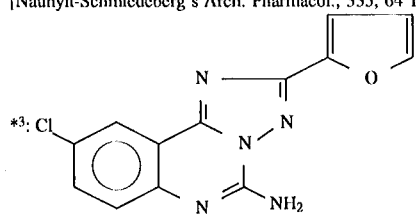

[J. Med. Chem., 31, 1014 (1988)]

Test Example 3, diuretic effect

Wistar rats (male: 150–300 g) were starved for 18 hours prior to the administration of the test compound. A test compound (25 mg/kg) and saline (25 ml/kg) were orally administered to test rats and only saline was administered to control rats. Three groups, each group consisting of 3 rats, were used for each test compound. Urine was collected for 6 hours after the administration. Urine volume was measured and the electrolytes ($Na^+$ and $K^+$) in the urine were determined with a flame photometer (775A, Hitachi Ltd., Japan). The results are shown in Table 3.

All parameters are expressed as relative values of control.

TABLE 3

| Compound No. | Increase in Urine (%) | Increase in $Na^+$ excretion (%) | Increase in $K^+$ excretion (%) | $Na^+/K^+$ |
|---|---|---|---|---|
| (Control) | 0 | 0 | 0 | 1.00 |
| 1 | 106 | 73 | 36 | 1.27 |
| 2 | 87 | 109 | 67 | 1.25 |
| 3 | 154 | 137 | 29 | 1.84 |
| 4 | 113 | 106 | 27 | 1.63 |
| 5 | 88 | 109 | 32 | 1.58 |
| 6*3 | 330 | 252 | 87 | 1.88 |
| 8 | 82 | 138 | 22 | 1.95 |
| 12 | 108 | 103 | 32 | 1.54 |
| 13 | 129 | 186 | 37 | 2.09 |

TABLE 3-continued

| Compound No. | Increase in Urine (%) | Increase in $Na^+$ excretion (%) | Increase in $K^+$ excretion (%) | $Na^+/K^+$ |
|---|---|---|---|---|
| 14 | 315 | 244 | 68 | 2.05 |
| 16 | 141 | 191 | 38 | 2.12 |
| 17 | 155 | 107 | 51 | 1.37 |
| 24 | 112 | 125 | 61 | 1.40 |
| 29 | 123 | 137 | 65 | 1.43 |
| 30 | 112 | 126 | 50 | 1.50 |
| 31 | 115 | 126 | 56 | 1.44 |
| 32 | 100 | 114 | 41 | 1.51 |
| 33 | 99 | 105 | 40 | 1.47 |
| Aminophylline*1 (Reference compound) | 34 | 89 | 17 | 1.62 |
| Furosemide*2 (Reference compound) | 75 | 64 | 57 | 1.07 |

*1 The Merck Index, 10th edition, page 476 (1983)
*2 The Merck Index, 10th edition, page 4189 (1983)
*3 The amount of the administration: 6.25 mg/kg Test Example 4, renal-protecting effect (glycerol-induced renal failure model).

A renal failure is a state where the renal function is lowered and the homeostasis of a body fluid can be no more maintained. It is known that an acute renal failure characteristic of uriniferous tubule disorder is caused by subcutaneous or intramuscular injection of glycerol to rats [Can. J. Physiol. Pharmacol., 65, 42 (1987)].

Male Wistar rats were kept deprived of water for 18 hours, and served for the test. A test compound was intraperitoneally administered to the rats (dosage: 1 ml/kg) and the rats were anesthetized with ether and 50% glycerol was subcutaneously administered (dosage: 0.8 ml/100 g) to the rats, pinching the dorsal skin. Twenty four hours after the administration of glycerol, the rats were anesthetized with ether and 5 ml of blood was collected from the abdominal aorta. The collected blood was allowed to stand for 30 minutes or longer and then centrifuged at 3,000 rpm for 10 minutes, and the amounts of the serum creatinine and urine-nitrogen (UN) contained in a serum were determined by auto analyzer (Olympus AU510) or measured by the creatinine test Wako (Jaffé method) and UN Test Wako (diacetylmonooxime direct method). Both are manufactured by Wako Pure Chemicals Co.

On the other hand, the left kidneys of the blood-sampled rats were removed and placed in formalin-filled vial bottles, and used as samples for the pathological examination.

According to the test results, Compound Nos. 1–5, 7, 8, 13, 14, 16, 17, 23, 25 and 31 significantly suppressed increases in the serum creatinine and in urine-nitrogen, when administered abdominally at a dosage of 0.01–10 mg/kg [i.p.] ($p<0.05$) whereas XAC and aminophylline had a weak effect of suppressing the increase, and PD 115,199 and CGS15,943 were totally invalid. On the contrary, furosemide showed a tendency to increase the serum creatinine. The pathological examination of removed kidneys indicates that compounds Nos. 1– 5, 7, 8, 13, 14, 16, 17, 23, 25 and 31 also significantly improved the state of kidneys.

Test Example 5, effects on passive Schultz-Dale reaction

Male Hartley guinea pigs weighing 350 to 500 g were passively sensitized by intraperitoneal injection of rabbit anti-egg white albumin (EWA) serum prepared by the method of Koda, et al. [Folia pharmacol, Japon 66,237 (1970)]. After 24 hours, the guinea pigs were stunned and exsanguinated, and then the trachea were removed. The zig-zag strips of the trachea were prepared by the method of Emmerson, et al. [J. Pharm. Pharmacol., 31, 798 (1979)]. The strips were suspended in Krebs-Henseleit solution at 37° C. aerated with 95% $O_2$ and 5% $CO_2$, and incubated for one hour. Antigen (EWA) was then introduced in the solution (final concentration; 1 μg/ml), and the contraction was measured by isotonictransducer (TD-112s, Nihon Kohden, Japan) and recorded on a recorder (Type 3066, Yokogawa-Hokushin Denki, Japan). After the contraction reached a stable plateau, the compounds were cumulatively added in order to get concentration-relaxation curves. Concentration of compounds to produce 50% relaxation ($IC_{50}$) was calculated from the regression curve, obtained from cumulative concentration-relaxation response. The results are shown in Table 4.

TABLE 4

| Compound No. | Passive S-D Reaction $IC_{50}$ (μM) | MED (mg/kg) for Inhibiting Death Induced by PAF |
|---|---|---|
| 7 | 2.7 | >100 |
| 8 | 0.88 | 100 |
| 25 | 17.3 | — |
| 26 | 22.7 | — |
| Theophylline | 23 | 100 |

Test Example 6, effect of inhibiting death induced by Platelet-Activating Factor (PAF)

A test compound (100 mg/kg) was orally administered to dd strain mice (male animals, 28 to 32 g) and 40 μg/kg of PAF (manufactured by Avanti Polar Lipids Co.) was administered via tail veins 1 hour after the administration according to the method of Carlson et al. [Agents and Actions, 21, 379 (1987)]. The mortality rates of compound-treated groups were compared with those of matched control groups, assessed during the same experimental session, by the Fisher's exact probability test. The cases wherein the level of significance (p value) is 0.05 or less are considered to be effective with respect to the inhibition. The above procedure was repeated, using the test compound in a decreasingly small quantity so as to find out the Minimum Effective Dosage (MED) wherein no significant difference be observed between the test and control groups.

The results are shown in Table 4.

Compound (I) or its pharmaceutically acceptable salts can be used as such or in various medicament forms. The present pharmaceutical composition can be prepared by uniformly mixing an effective amount of Compound (I) or its pharmaceutically acceptable salts as an active component with a pharmaceutically acceptable carrier. The pharmaceutical composition is desirably in a unit dosage form applicable to oral or injection administration.

In the preparation of pharmaceutical compositions in an oral dosage form, some useful, pharmaceutically acceptable carrier can be used. For example, liquid, orally administerable compositions such as suspension compositions or syrup compositions can be prepared with water, a saccharide such as sucrose, sorbitol, fructose, etc., a glycol such as polyethyleneglycol, propyleneglycol, etc., an oil such as sesame oil, olive oil, soybean oil, etc., an antiseptic such as p-hydroxybenzoic acid esters, etc., and a flavor such as strawberry flavor, peppermint, etc. Powder, pills, capsules and tablets can be prepared with a vehicle such as lactose, glucose, sucrose, mannitol, etc., a disintegrator such as starch, sodium alginate, etc., a lubricant such as magnesium stearate, talc, etc., a binder such as polyvinyl alcohol, hydroxypropyl cellulose, gelatin, etc., a surfactant such as fatty acid esters, etc., a plasticizer such as glycerin, etc. and so forth. Tablets and capsules are most useful unit for oral administration because of easy administration. In the preparation of tablets or capsules, a solid pharmaceutical carrier is used.

Injection solutions can be prepared with a carrier such as distilled water, saline solution, glucose solution, or a mixture of saline solution and glucose solution.

Effective dosage and number of administration of Compound (I) or its pharmaceutically acceptable salts depend on the administration route and ages, body weights, symptoms, etc. of patients, and it is preferable to usually administer Compound (I) at a dosage of 1 to 50 mg/kg per day in 3 to 4 divisions.

Compound (I) and pharmacologically acceptable salts thereof can also be administered by inhalation in the form of aerosol, finely divided powders or sprayed mist. In the case of aerosol administration, the compounds according to the invention can be dissolved in an appropriate, pharmacologically acceptable solvent (e.g., ethyl alcohol) or a mixture of miscible solvents, and then admixed with a pharmacologically acceptable propellant. Such an aerosol composition can be charged in a pressure container equipped with an appropriate aerosol valve suited for the spraying of the aerosol composition. It can be preferable to use an aerosol valve which is capable of spraying a predetermined quantity of aerosol composition to provide an effective dosage thereof.

The present invention will be described below, by the following Examples and Reference Examples.

EXAMPLE 1

8-[(1R*,4S*,5S*)
-2-Bicyclo[2.2.1]hepten-5-yl]-1,3-dipropylxanthine
(Compound 1) and 8-[(1R*,4S*,5R*)-2
-bicyclo[2.2.1]hepten-5-yl]-1,3-dipropylxanthine
(Compound 2)

At first, 2.57 g (18.6 mmol) of bicyclo[2,2,1]-5 -heptane-2-carboxylic acid and 3.06 g (16.0 mmol) of 1-ethyl-3-(3-dimethylaminopropyl)carbodiimide hydrochloride were added to a solution of 3.00 g (13.3 mmol) of 1,3-dipropyl-5,6 -diaminouracil [U.S. Pat. No. 2,607,295 and J. Org. Chem., 16, 1879 (1951)] in 60 ml of dioxane and 30 ml of water and the mixture was stirred at room temperature for 1 hour, while adjusting the pH to 5.5. The pH of the mixture is adjusted to 7.0, and the mixture was extracted with chloroform three times, and the extract was washed with a saturated aqueous sodium chloride and dried over anhydrous sodium sulfate. Then, the solvent was evaporated under reduced pressure and the residue was purified by silica gel column chromatography (eluent: 2.0% methanol/chloroform) to afford 4.07 g (yield: 88%) of amorphous 6-amino-5-(2-bicyclo[2,2,1]hepten-5 -yl)carbonylamino-1,3-dipropyluracil.

NMR (CDCl$_3$, 90 MHz) δ (ppm): 7.20 (brs, 1H), 6.22–5.95 (m, 2H), 5.35 (brs, 2H), 4.00–3.65 (m, 4H), 3.52–2.80 (m, 3H) and 2.20–0.80 (m, 14H)

Then, 40 ml of dioxane and 40 ml of 2N sodium hydroxide aqueous solution were added to 3.99 g (11.5 mmol) of the thus obtained compound and the mixture was refluxed under heating for 20 minutes. After cooling, the mixture was neutralized and extracted with chloroform three times. Then, the extract was washed with a saturated aqueous sodium chloride and dried over anhydrous sodium sulfate, and then the solvent was evaporated under reduced pressure. The residue was purified by silica gel column chromatography (eluent: 25% ethyl acetate/hexane) and recrystallized from cyclohexane to afford 1.97 g (yield: 52%) of the captioned Compound 1 as a white powder and 0.63 g (yield: 18%) of the captioned Compound 2 as a white powder.

Compound 1:

Melting point: 121.6°–122.8° C. (recrystallized from isopropanol/water) Rf value: 0.30 [TLC plate silica gel 60F$_{254}$ (product of Merck Co., eluent: 30% ethylacetate/hexane] Elemental analysis: C$_{18}$H$_{24}$N$_4$O$_2$ Calculated (%): C 65.83, H 7.37, N 17.06 Found (%) : C 65.71, H 7.51, N 16.78 IR (KBr) vmax (cm$^{-1}$): 1,698, 1,653, 1,497 NMR (DMSO-d$_6$) δ (ppm): 12.84 (s, 1H), 6.17 (dd, J=3.2, 5.6 Hz, 1H), 5.72 (dd, J=2.7, 5.6 Hz, 1H), 3.91 (t, 2H), 3.82 (t, 2H), 3.43 (ddd, J=4.2, 4.2, 9.3 Hz, 1H), 3.28 (brs, 1H), 2.92 (brs, 1H), 2.08 (ddd, J=3.7, 9.3, 13.0 Hz, 1H), 1.75–1.50 (m, 5H), 1.45–1.35 (m, 2H) and 0.90–0.80 (m, 6H)

Compound 2:

Melting point: 167.6°–168.0° C. (recrystallized from ethanol/water) Elemental analysis: C$_{18}$H$_{24}$N$_4$O$_2$ Calculated (%): C 65.83, H 7.37, N 17.06 Found (%) : C 66.03, H 7.69, N 17.09 Rf value: 0.46 (30% ethyl acetate/hexane) IR (KBr) vmax (cm$^{-1}$): 1,695, 1,657, 1,495 NMR (DMSO-d$_6$) δ (ppm): 13.11 (brs, 1H), 6.21 (d, J=1.4 Hz, 2H), 3.95 (t, 2H), 3.84 (t, 2H), 2.96 (brs, 2H), 2.63 (ddd, J=0.7, 4.2, 8.2 Hz, 1H), 2.10 (ddd, J=4.2, 4.2, 11.5 Hz, 1H), 1.75–1.45 (m, 5H), 1.35–1.22 (m, 2H), 0.92–0.80 (m, 6H).

EXAMPLE 2

8-[(1R*,2S*,5S*)-Bicyclo[2,2,1]heptan-2-yl]-1,3-dipropylxanthine (Compound 3) and
8-[(1R*,2R*,5S*)-bicyclo[2.2.1]heptan-2-yl]-1,3-dipropylxanthine (Compound 4)

The substantially same operations as in Example 1 were repeated using 3.0 g (13.3 mmol) of 1,3-dipropyl-5,6-diaminouracil and 2.61 g (18.6 mmol) of bicyclo[2.2.1]heptane-2-carboxylic acid to afford 4.31 g (yield: 93%) of amorphous 6 -amino-5-(bicyclo[2.2.1]heptan-2-yl)carbonylamino-1,3-dipropyluracil.

NMR (CDCl$_3$, 90 MHz) δ (ppm): 7.21 (brs, 1H), 5.40 (brs, 2H), 4.00–3.70 (m, 4H), 3.00–2.75 (m, 1H), and 2.65–0.75 (m, 20H)

The substantially same cyclization reaction as in Example 1 was performed using 4.30 g (12.3 mmol) of the thus obtained compound, to afford 3.05 g (yield: 75%) of 8-bicyclo[2.2.1]heptan-2-yl)-1,3-dipropylxanthine [a mixture of (1R*,2S*,5S*) isomer (Compound 3) and (1R*,2R*,5S*) isomer (Compound 4)] as a white powder. The mixture was subjected to high performance liquid chromatography (HPLC) [column, R-354 (30 cm×50 mmφ) (by Yamamura Kagaku K.K.); eluent, 85% methanol/water; flow rate, 50 ml/min.] to afford 327 mg of the captioned Compound 3 and 442 mg of the captioned Compound 4.

Compound 3:

Melting point: 150.9°–152.0° C. (recrystallized from isopropanol/water) Elementary analysis: C$_{18}$H$_{26}$N$_4$O$_2$ Calculated (%): C 65.43, H 7.93, N 16.96 Found (%) : C 65.41, H 8.11, N 17.00 IR (KBr) vmax (cm$^{-1}$): 1700, 1650, 1497. NMR (DMSO-d$_6$) δ (ppm): 13.00 (brs, 1H), 3.97 (t, 2H), 3.84 (t, 2H), 3.21 (ddd, J=4.2, 4.2, 11.6 Hz, 1H), 2.55 (brs, 1H), 2.28 (brs, 1H), 1.90–1.22 (m, 11H), 1.15–1.03 (m, 1H), 0.95–0.82 (m, 6H). HPLC [AM-312 (15 cm×5 mmφ) (by Yamamura Kagaku K.K.), acetonitrile-water, UV 254 nm, 1.0 ml/min]: 70% Retention time; 12.7 min.

Compound 4:

Melting point: 139.7°–142.9° C. (recrystallized from isopropanol/water) Elementary analysis: C$_{18}$H$_{26}$N$_4$O$_2$ Calculated (%): C 65.43, H 7.93, N 16.96 Found (%) C 65.66, H 8.29, N 16.90 IR (KBr) vmax (cm$^{-1}$): 1702, 1650, 1494. NMR (DMSO-d$_6$) δ (ppm): 12.99 (brs, 1H), 3.94 (t, 2H), 3.83 (t, 2H), 2.79 (dd, J=4.9,8.5 Hz, 1H), 2.39 (brs, 1H), 2.31 (brs, 1H), 2.08–1.96 (m, 1H), 1.80–1.45 (m, 8H), 1.38–1.12 (m, 3H), 0.95–0.80 (m, 6H). HPLC [AM-312 (15 cm×5 mmφ) (by Yamamura Kagaku K.K.) 70% acetonitrile-water, UV 254 nm, 1.0 ml/min]: Retention time; 13.9 min.

In Examples 3 to 9 described below, the desired compounds were obtained in the substantially same operations as in Example 1, except that a corresponding carboxylic acid was used instead of bicyclo[2.2.1]-5-hepten-2-carboxylic acid. In those examples, intermediates obtained were used in the subsequent cyclization reactions without being isolated or purified.

EXAMPLE 3

8-[(1R*,2R*,5R*)-Bicyclo[3.3.0]octan-2-yl]-1,3-dipropylxanthine (Compound 5) and
8-[(1R*,2S*,5R*)-bicyclo[3.3.0]oxtan-2-yl]-1,3-dipropylxanthine (Compound 6)

The substantially same operations as in Example 1 were repeated using 4.55 ml (31.9 mmol) of bicyclo[3.3.0]octane-2-carboxylic acid, and the following two compounds were obtained.

Compound 5:

Yield: 4.30 g (Yield, 47%; white plate crystal) Melting point: 100.1°–101.6° C. (recrystallized from heptane) Rf value: 0.53 (30% ethyl acetate/hexane) Elementary analysis: $C_{19}H_{28}N_4O_2$ Calculated (%): C 66.25, H 8.19, N 16.27 Found (%) C 66.07, H 8.43, N 16.61 IR (KBr) vmax (cm$^{-1}$): 1,699, 1,653 and 1,499 NMR(DMSO-d$_6$) δ (ppm): 13.12 (brs, 1H), 3.94 (t, 2H), 3.83 (t, 2H), 2.75–2.50 (m, 3H), 2.10–1.45 (m, 12H), 1.42–1.35 (m, 1H), 1.30–1.15 (m, 1H), 0.95–0.85 (m, 6H) $^{13}$C-NMR (CDCl$_3$) δ (ppm): 159.1, 155.7, 151.1, 149.4, 106.7, 50.4, 47.6, 45.3, 43.4, 43.2, 34.4, 34.1, 33.6, 32.1, 25.1, 21.4, 11.4, 11.2.

Compound 6:

Yield: 359 mg (Yield, 3.9%; white plate crystal) Melting point: 118.4°–120.0° C. (recrystallized from heptane) Rf value: 0.40 (30% ethyl acetate/hexane) Elementary analysis: $C_{19}H_{28}N_4O_2$ Calculated (%): C 66.25, H 8.19, N 16.27 Found (%) C 66.20, H 8.63, N 16.31 IR (KBr) vmax (cm$^{-1}$): 1,699, 1,652 and 1,497 NMR (CDCl$_3$) δ (ppm): 12.30 (brs, 1H), 4.11 (t, 2H), 4.02 (t, 2H), 3.30 (ddd, 1H, J=6.8, 14 Hz), 3.00–2.85 (m, 1H), 2.70–2.53 (m, 1H), 2.25–0.90 (m, 20H) $^{13}$C-NMR (CDCl$_3$) δ (ppm): 157.0, 155.5, 151.2, 149.2, 106.5, 47.6, 45.2, 44.0, 43.3, 42.9, 35.4, 32.5, 29.7, 27.5, 27.4, 21.4, 21.4, 11.4, 11.2. MS (m/e) relative intensity: 344 (M$^+$, 100), 302 (28), 260 (18), 250 (23) and 230 (18)

EXAMPLE 4

8-[1-methyl-2-(4-pyridyl)ethyl]-1,3-dipropylxanthine (Compound 7)

Overall yield: 79% (White needle crystal) Melting point: 214.9°–217.3° C. Elementary analysis: $C_{19}H_{25}N_5O_2$·HCl·0.1H$_2$O Calculated (%): C 57.74, H 6.64, N 17.72 Found (%) C 57.79, H 6.54, N 17.63 IR (KBr) vmax (cm$^{-1}$): 1,704, 1,669 and 1,637 NMR (DMSO-d$_6$) δ (ppm): 13.50–12.80 (brs, 1H), 8.79 (d, 2H, J=6.1 Hz), 7.84 (d, 2H, J=6.1 Hz), 3.90 (t, 2H), 3.81 (t, 2H), 3.50–3.20 (m, 3H), 1.70–1.50 (m, 4H), 1.33 (d, 3H, J=6.7 Hz), 0.85 (t, 3H), 0.82 (t, 3H)

EXAMPLE 5

8-[1-Methyl-2-(2-methylthiazol-4-yl)ethyl]-1,3-dipropylxanthine (Compound 8)

Overall yield: 70% (White plate crystal) Melting point: 137.6°–139.2° C. (recrystallized from cyclohexane) Elementary analysis: $C_{18}H_{25}N_5O_2S$ Calculated (%): C 57.58, H 6.71, N 18.65 Found (%) C 57.75 H 6.72, N 18.48 IR (KBr) vmax (cm$^{-1}$): 1,698, 1,659 and 1,499 NMR (DMSO-d$_6$) δ (ppm): 13.11 (brs, 1H), 7.00 (s, 1H), 3.94 (t, 2H), 3.83 (t, 2H), 3.45–3.10 (m, 3H), 2.92 (dd, 1H, J×6.8, 14.2 Hz), 2.59 (s, 3H), 1.75–1.50 (m, 4H), 1.23 (d, 3H, J=6.8 Hz), 0.95–0.80 (m, 6H)

EXAMPLE 6

8-(Benzo[b]thiophen-2-yl)-1,3-dipropylxanthine (Compound 9)

Overall yield: 61% (White needle crystal) Melting point: 307.9°–309.1° C. (recrystallized from ethanol) Elementary analysis: $C_{19}H_{20}N_4O_2S$ Calculated (%): C 61.94, H 5.47, N 15.21 Found (%) C 61.91, H 5.44, N 15.15 IR (KBr) vmax (cm$^{-1}$): 1,699, 1,642 and 1,537 NMR (DMSO-d$_6$) δ (ppm): 8.19 (s, 1H), 8.05–7.85 (m, 2H), 7.50–7.40 (m, 2H), 4.00 (t, 2H), 3.87 (t, 2H), 1.85–1.50 (m, 4H), 1.00–0.80 (m, 6H)

EXAMPLE 7

8-(Benzo[b]furan-2-yl)-1,3-dipropylxanthine (Compound 10)

Overall yield: 71% (White needle crystal) Melting point: 282.1°–283.9° C. (recrystallized from ethanol) Elementary analysis: $C_{19}H_{20}N_4O_3$ Calculated (%): C 64.76, H 5.72, N 15.90 Found (%): C 64.80, H 5.72, N 15.77 IR (KBr) vmax (cm$^{-1}$): 1,700 and 1,648 NMR (DMSO-d$_6$) δ (ppm): 14.30 (brs, 1H), 7.80–7.65 (m, 2H), 7.68 (s, 1H), 7.50–7.30 (m, 2H), 4.02 (t, 2H), 3.88 (t, 2H), 1.85–1.50 (m, 4H), 1.00–0.80 (m, 6H)

EXAMPLE 8

8-(3-Methylinden-2-yl)-1,3-dipropylxanthine (Compound 11)

Overall yield: 36% (Light yellow plate crystal) Melting point: 268.1°–269.9° C. (recrystallized from ethanol) Elementary analysis: $C_{21}H_{24}N_4O_2$ Calculated (%): C 69.21, H 6.64, N 15.37 Found (%) C 69.40, H 6.72, N 15.34 IR (KBr) vmax (cm$^{-1}$): 1,690, 1,641 and 1,485 NMR (DMSO-d$_6$) δ (ppm): 13.33 (brs, 1H), 7.55–7.45 (m, 2H), 7.40–7.25 (m, 2H), 4.04 (t, 2H), 3.88 (s, 2H), 3.90–3.80 (m, 2H), 2.61 (s, 3H), 1.85–1.50 (m, 4H), 0.95–0.80 (m, 6H)

EXAMPLE 9

8-(2-Aminothiazol-4-yl)methyl-1,3-dipropylxanthine (Compound 12)

Overall yield: 94% (Light yellow plate crystal) Melting point: 282.5°–284.3° C. (recrystallized from isopropanol) IR (KBr) vmax (cm$^{-1}$): 1,697, 1,660, 1,523 and 1,500 NMR (DMSO-d$_6$) δ (ppm): 13.28 (brs, 1H), 6.89 (brs, 2H), 6.23 (s, 1H), 4.00–3.80 (m, 4H), 3.86 (s, 2H), 1.80–1.50 (m, 4H), 0.95–0.80 (m, 6H) MS (m/e) (Relative intensity): 348 (M$^+$, 100), 306 (51), 277 (26), 264 (47), 248 (28), 234 (86) and 113 (38)

EXAMPLE 10

8-(Noradamantan-3-yl)-1,3-dipropylxanthine (Compound 14)

At first, 1.62 g (9.74 mmol) of 3-noradamantanecarboxylic acid was dissolved in 30 ml of pyridine, and 0.78. ml (10.7 mmol) of thionyl chloride was gradually added thereto at 0° C. After the mixture was stirred for 30 minutes at room temperature, 2.00 g (8.85 mmol) of 1,3-dipropyl-5,6-diaminouracil was gradually added thereto at 0° C. After stirring for 30 minutes at 0° C., the mixture was treated in the same procedure as in Example 29, and the residue was subjected to silica gel column chromatography (eluent: 1% methanol/chloroform) to afford 3.55 g (yield: 100%) of amorphous 6-amino-5-(noradamantane-3-carbonylamino)-1,3-dipropyluracil.

NMR (90 MHz; CDCl$_3$) δ (ppm): 7.38 (brs, 1H), 5.62 (brs, 2H), 4.00–3.70 (m, 4H), 2.90–2.60 (m, 1H), 2.40–1.30 (m, 16H), 1.10–0.80 (m, 6H)

The substantially same cyclization reaction as in Example 29 was performed by reacting 2.90 g (7.55 mmol) of the thus obtained compound with phosphorus oxychloride to afford 509 mg (yield: 14%) of the captioned Compound 14 as a white needle crystal.

Melting point: 190.0°–191.0° C. (recrystallized from heptane) Elementary analysis: $C_{20}H_{28}N_4O_2$ Calculated (%): C 67.39, H 7.92, N 15.72 Found (%) C 67.41, H 7.62, N 15.78 IR (KBr) vmax (cm$^{-1}$): 1,699, 1,651 and 1,499 NMR (DMSO-d$_6$) δ (ppm): 12.97 (s, 1H), 3.95(t, 2H), 3.85 (t, 2H), 2.70–2.60 (m, 1H), 2.35–2.26 (m, 2H), 2.20–2.10 (m, 2H), 1.95–1.82 (m, 4H), 1.80–1.50 (m, 8H), 0.95–0.80 (m, 6H) $^{13}$C-NMR (DMSO-d$_6$) δ (ppm): 159.9, 153.9, 150.7, 147.6, 106.6, 48.8, 48.2, 45.1, 44.2, 43.2, 41.9, 36.9, 34.1, 20.8, 11.1, 10.9.

EXAMPLE 11

8-(Adamantan-1-yl)methyl-1,3-dipropylxanthine (Compound 15)

At first 2.00 g (8.85 mmol) of 1,3-dipropyl-5,6-diaminouracil and 2.06 g (10.6 mmol) of 1-adamantaneacetic acid were condensed according to the procedure of Example 1 using 1-ethyl-3-(3-dimethylaminopropyl)carbodiimide to afford 4.02 g (yield: 100%) of amorphous 6-amino-5-(adamantan-1-yl)acetylamino-1,3-dipropyluracil as a crude product.

NMR (CDCl$_3$) δ (ppm): 7.42 (brs, 1H), 5.47 (brs, 2H), 4.00–3.70 (m, 4H), 2.20–1.20 (m, 21H), 1.10–0.80 (m, 6H)

The substantially same cyclization reaction as in Example 29 was performed by reacting 3.95 g of the thus obtained compound with phosphorus oxychloride to afford 1.66 g (overall yield: 49%) of the captioned Compound 15 as a white needle crystal. Melting point: 177.7°–179.5° C. (recrystallized from isopropanol/water) Elementary analysis: $C_{22}H_{32}N_4O_2$ Calculated (%): C 68.72, H 8.39, N 14.57 Found (%) C 68.71, H 8.74, N 14.70 IR (KBr) vmax (cm$^{-1}$): 1,704, 1,648 and 1,498 NMR (DMSO-d$_6$) δ (ppm): 13.06 (brs, 1H), 3.95 (t, 2H), 3.83 (t, 2H), 3.40–3.25 (m, 2H), 2.43 (brs, 2H), 1.90 (brs, 3H), 1.80–1.45 (m, 16H), 0.95–0.85 (m, 6H)

EXAMPLE 12

8-[(1R*,2R*,5S*)-Bicyclo[2.2.1]heptan-2-yl]methyl-1,3-dipropyloxanthine (Compound 16)

Compound 16 was obtained in the same procedure as in Example 11, except for using 1.54 ml (10.6 mmol) of (1R*,2R*,5S*)-bicyclo[2.2.1]heptane-2-acetic acid in place of 1-adamantaneacetic acid.

Yield: 1.22 g (White needle crystal; overall yield, 40%) Melting point: 119.9°–121.4° C. (recrystallized from isopropanol/water) Elementary analysis: $C_{19}H_{28}N_4O_2$ Calculated (%): C 66.25, H 8.19, N 16.27 Found (%) C 66.29, H 8.32, N 16.06 IR (KBr) vmax (cm$^{-1}$): 1,699, 1,654 and 1,502 NMR (CDCl$_3$) δ (ppm): 12.83 (brs, 1H), 4.15–4.00 (m, 4H), 2.81 (dd, 1H, J=7.8, 14.2 Hz), 2.66 (dd, 1H, J=7.8, 14.2 Hz), 2.26 (brs, 1H), 2.15–2.00 (m, 2H), 1.95–1.65 (m, 4H), 1.60–1.40 (m, 4H), 1.30–0.90 (m, 10H)

EXAMPLE 13

8-[(1R*,4S*,5S*)-2-Bicyclo[2.2.1]hepten-5-yl]-1,3-dipropyl-7-methylxanthine (Compound 17)

At first 1.00 g (3.05 mmol) of 8-[(1R*,4S*,5S*)-2bicyclo[2.2.1]hepten-5-yl]-1,3-dipropylxanthine (Compound 1) prepared in Example 1 was dissolved in 30 ml of N,N'-dimethylformamide, and 1.05 g (7.61 mmol) of potassium carbonate and 0.38 ml (6.10 mmol) of methyl iodide were added thereto. After the mixture was stirring at 50° C. for 30 minutes under argon atmosphere, insoluble materials were filtered off, and the filtrate was concentrated under reduced pressure. The residue was poured into 200 ml of water and the mixture was extracted with chloroform three times. The organic layer was combined, and the extract was washed with water and then with a saturated aqueous sodium chloride, and dried over anhydrous sodium sulfate and then the solvent was evaporated under reduced pressure. The residue was subjected to silica gel column chromatography (eluent: 20% ethyl acetate/hexane) to afford 1.05 g (yield: 100%) of the captioned Compound 17 as a light yellow powder.

Melting point: 99.8°–103.1° C. (recrystallized from acetone/water) Elementary analysis: $C_{19}H_{26}N_4O_2$ Calculated (%): C 66.64, H 7.65, N 16.36 Found (%) C 66.60, H 7.97, N 16.55 IR (KBr) vmax (cm$^{-1}$): 1698, 1666, 1652, 1445. NMR (CDCl$_3$) δ (ppm): 6.19 (dd, J=3.0, 5.6 Hz, 1H), 5.87 (dd, J=2.8, 5.6 Hz, 1H), 4.01 (t, 2H), 3.95 (t, 2H), 3.94 (s, 3H), 3.36–3.28 (m, 2H), 3.00 (brs, 1H), 2.19 (ddd, J=3.9, 9.3, 11.5 Hz, 1H), 1.84–1.50 (m, 6H), 1.45–1.40 (m, 1H), 1.00–0.90 (m, 6H).

EXAMPLE 14

8-[(1R*,2R*,5R*)-Bicyclo[3.3.0]octan-2-yl]-1,3-dipropyl-7-methylxanthine (Compound 18)

The substantially same operations as in Example 13 were repeated except for using 1.00 g (2.90 mmol) of 8-8(1R*,2R*,5R*)-bicyclo[3.3.0]octan-2-yl]-1,3-dipropylxanthine (Compound 5) prepared in Example 3 to afford 1.05 g (yield: 100%) of the captioned Compound 18 as a white powder.

Melting point: 94.7°–97.0° C. (recrystallized from ethanol/water) Elementary analysis: $C_{20}H_{30}N_4O_2$ Calculated (%): C 67.01, H 8.44, N 15.63 Found (%) C 66.93, H 8.20, N 15.68 IR (KBr) vmax (cm$^{-1}$): 1702, 1653. NMR (CDCl$_3$) δ (ppm): 4.05 (t, 2H), 3.96 (t, 2H), 3.93 (s, 3H), 2.96–2.84 (m, 1H), 2.80–2.64 (m, 2H), 2.20–1.60 (m, 11H), 1.48–1.25 (m, 3H), 1.02–0.94 (m, 6H).

EXAMPLE 15

1,3-Dipropyl-7-methyl-8-(noradamantan-3-yl)xanthine (Compound 20)

The substantially same operations as in Example 13 were repeated except for using 2.20 g (6.18 mmol) of 8-(noradamantan-3-yl)-1,3-dipropylxanthine (Compound 14) prepared in Example 10 to afford 1.06 g (yield: 46%) of the captioned Compound 20 as a white needle crystal.

Melting point: 123.2°–124.8° C. (recrystallized from ethanol/water) Elementary analysis: $C_{21}H_{30}N_4O_2$ Calculated (%): C 68.08, H 8.16, N 15.12 Found (%) C 67.93, H 8.23, N 15.44 IR (KBr) vmax (cm$^{-1}$): 1698, 1661. NMR (CDCl$_3$) δ (ppm): 4.05 (t, 2H), 4.01 (s, 3H), 3.96 (t, 2H), 2.98(t, 2H), 2.40 (brs, 2H), 2.25–2.17 (m, 2H), 2.11–1.90 (m, 6H).

EXAMPLE 16

7-Ethyl-1,3-dipropyl-8-(noradamantan-3-yl)xanthine (Compound 21)

The substantially same operations as in Example 13 were repeated except for using 1.40 g (3.93 mmol) of 8-(noradamantan-3-yl)-1,3-dipropylxanthine (Compound 14) prepared in Example 10 and 0.62 ml (7.87 mmol) of ethyl iodide to afford 410 mg (yield: 27%) of the captioned Compound 21 as a white crystal.

Melting Point: 91.3°–92.4° C. (recrystallized from acetonitrile) Elementary analysis: $C_{22}H_{32}N_4O_2$ Calculated (%): C 68.71, H 8.38, N 14.57 Found (%) C 68.88, H 8.59, N 14.69 IR (KBr) νmax (cm$^{-1}$): 1698, 1661, 1535. NMR (CDCl$_3$, 90 MHz) δ (ppm): 4.34 (q, J=7.0 Hz, 2H), 4.20–3.86 (m, 4H), 3.03 (t, 1H), 2.50–1.40 (m, 16H), 1.50 (t, J=7.0 Hz, 3H), 1.15–0.85 (m, 6H).

EXAMPLE 17

8-(Noradamantan-3-yl)-1,3,7-tripropylxanthine (Compound 22)

The substantially same operations as in Example 13 were repeated except for using 1.50 g (4.21 mmol) of 8-(noradamantan-3-yl)-1,3-dipropylxanthine (Compound 14) prepared in Example 10 and 0.82 ml (8.43 mmol) of propyl iodide to afford 1.40 g (yield: 84%) of the captioned Compound 22 as a white crystal.

Melting point: 111.2°–112.2° C. (Recrystallized from ethanol/water) Elementary analysis: $C_{23}H_{34}N_4O_2$ Calculated (%): C 69.31, H 8.59, N 14.05 Found (%) C 69.29, H 8.69, N 14.57 IR (KBr) νmax (cm$^{-1}$): 1700, 1662, 1536. NMR (CDCl$_3$, 90 MHz) δ (ppm): 4.30–3.85 (m, 6H), 3.05 (t, 1H), 2.50–1.50 (m, 18H), 1.20–0.85 (m, 6H).

EXAMPLE 18

8-[(1R*,2R*,5R*)-Bicyclo[3.3.0]octan-2-yl]-3-propylxanthine (Compound 23)

At first, 100 ml of N,N'-dimethylformamide was suspended in 5.00 g (27.2 mmol) of 5,6-diaminouracil [Japanese Published Unexamined Patent Application No. 57,517/80] and 3.88 ml (27.2 mmol) of bicyclo[3.3.0]octan-2-carboxylic acid, 8.40 g (40.8 mmol) of N,N'-dicyclohexylcarbodiimide and then 5.00 g (32.6 mmol) of N-hydroxybenztriazole were added thereto. After the mixture was stirred overnight at room temperature, insoluble materials were filtered off, and the filtrate was concentrated under reduced pressure. 100 ml of aqueous 4N sodium hydroxide solution was added to the residue, and the mixture was refluxed under heating for 20 minutes. After cooling, the mixture was neutralized with concentrated hydrochloric acid, and the precipitated crystals were collected by filtration. 500 ml of water was added to the resulting crystals, and the mixture was extracted with chloroform three times. The combined extract was washed with a saturated aqueous sodium chloride and dried over anhydrous sodium sulfate, and then the solvent was evaporated under reduced pressure. The obtained crude crystals were recrystallized from ethanol-water to afford 3.68 g (yield: 45%) of the captioned Compound 23 as a white needle crystal.

Melting point: 252.8°–257.9° C. (recrystallized from ethanol/water) Elementary analysis: $C_{16}H_{22}N_4O_2$ Calculated (%): C 63.55, H 7.33, N 18.53 Found (%) C 63.40, H 7.67, N 18.88 IR (KBr) νmax (cm$^{-1}$): 1700, 1678. NMR (DMSO-d$_6$) δ (ppm): 13.03 (brs, 1H), 10.88 (brs, 1H), 3.87 (t, 2H), 2.72–2.50 (m, 3H), 2.10–1.15 (m, 12H), 0.87 (t, 3H).

EXAMPLE 19

8-[(1R*,2R*,5R*)-Bicyclo[3.3.0]octan-2-yl]-1,3-dipropyl-2-thioxanthine (Compound 24)

The substantially same operations as in Example 1 were repeated except for using 2.00 g (8.26 mmol) of 5,6-diamino-1,3-dipropyl-2-thiouracil [J. Med. Chem., 32, 1873 (1989)] and 1.42 ml (9.92 mmol) of bicyclo[3.3.0]octan-2-carboxylic acid to afford 1.70 g (overall yield: 57%) of the captioned Compound 24 as a white crystal.

Melting point: 135.1°–137.2° C. (recrystallized from ethanol) Elementary analysis: $C_{19}H_{28}N_4OS$ Calculated (%): C 63.30, H 7.83, N 15.54 Found (%) C 63.54, H 8.14, N 15.59 IR (KBr) νmax (cm$^{-1}$): 1688, 1493. NMR (CDCl$_3$) δ (ppm): 12.68 (brs, 1H), 4.68 (t, 2H), 4.63 (t, 2H), 2.92–2.65 (m, 3H), 2.25–1.53 (m, 12H), 1.50–1.43 (m, 1H), 1.41–1.22 (m, 1H), 1.15–0.98 (m, 6H). HPLC [AM-312 (15 cm×5 mmø) (by Yamamura Kagaku K.K.), 70% acetonitrile-water, UV 254 nm, 2.0 ml/min]: Retention time; 14.4 min.

EXAMPLE 20

8-(Noradamantan-3-yl)-3-propylxanthine (Compound 25)

The substantially same operations as in Example 10 were repeated except for using 2.00 g (10.9 mmol) of 1-propyl-5,6-diaminouracil to afford 2.27 g (yield: 63%) of 6-amino-5-(noradamantane-3-carbonylamino)-3-propyluracil as a light yellow powder.

NMR (DMSO-d$_6$, 90 MHz) δ (ppm): 10.47 (brs. 1H), 7.63 (brs, 1H), 6.23 (brs, 2H), 3.78 (t, 2H), 2.71 (t, 1H), 2.32–1.38 (m, 14H), 0.89 (t, 3H).

The substantially same cyclization reaction as in Example 1 was performed using 2.16 g (6.51 mmol) of the thus obtained compound and 40 ml of a 2N sodium hydroxide aqueous solution to afford 1.85 g (yield: 91%) of the captioned Compound 25 as a white crystal.

Melting point: >290° C. (from dioxane/water) Elementary analysis: $C_{17}H_{22}N_4O_2$ Calculated (%): C 64.94, H 7.05, N 17.82 Found (%) C 64.65, H 7.20, N 18.00 IR (KBr) νmax (cm$^{-1}$): 1698, 1660, 1500. NMR (DMSO-d$_6$, 90 MHz) δ (ppm): 12.42 (brs, 1H), 11.90 (brs, 1H), 4.08 (t, 2H), 2.77 (t, 1H) 2.55–1.40 (m, 14H), 1.00 (t, 3H).

EXAMPLE 21

8-(Noradamantan-3-yl)-3-propyl-6-thioxanthine (Compound 26)

At first, 20.0 g (63.7 mmol) of 8-(noradamantan-3-yl)-3-propylxanthine (Compound 25) prepared in Example 20 was dissolved in 370 ml of pyridine, and 23.1 g (104 mmol) of phosphorus pentasulfide was added thereto. The mixture was refluxed under heating for 4 hours and poured into ice water, and the solid substances deposited were collected by filtration. The filtrate was concentrated under reduced pressure, and the solid substances deposited were again collected by filtration. The deposited solid substances were combined and dissolved in 200 ml of 2N sodium hydroxide solution, and insoluble materials were filtered off. The filtrate was neutralized with concentrated hydrochloric acid, and the deposited crystals were collected by filtration. The crude crystals were recrystallized from ethanol-water to afford 11.7 g (yield: 56%) of the captioned Compound 26 as a light yellow needle crystal.

Melting point: 214.2°–216.0° C. (recrystallized from ethanol/water) Elementary analysis: $C_{17}H_{22}N_4OS \cdot 1/5H_2O$ Calculated (%): C 61.12, H 6.76, N 16.77 Found (%) C 61.12, H 6.82, N 16.95 IR (KBr) νmax (cm$^{-1}$): 1668, 1595. NMR (CDCl$_3$, 90 MHz) δ (ppm): 10.14 (brs, 1H), 9.43 (brs, 1H), 4.05 (t, 2H), 2.73 (t, 1H), 2.68–1.40 (m, 14H), 0.98 (t, 3H).

EXAMPLE 22

8-(Noradamantan-3-yl)-1,3-dimethylxanthine (Compound 27)

The substantially same operations as in Example 10 were repeated except for using 3.00 g (17.6 mmol) of 1,3-dimethyl-5,6-diaminouracil instead of 1,3-dipropyl-5,6-diaminouracil [J. Am. Chem. Soc., 76, 2798 (1954)] to afford 3.61 g (yield: 65%) of 6-amino-5-(noradamantane-3-carbonylamino)-1,3-dimethyluracil as a light yellow powder.

NMR (DMSO-$d_6$, 90 MHz) δ (ppm): 7.68 (brs, 1H), 6.28 (brs, 2H), 3.30 (s, 3H), 3.11 (s, 3H), 2.71 (t, 1H), 2.66–1.40 (m, 12H).

The substantially same cyclization reaction as in Example 1 was performed except for using 3.60 g (11.3 mmol) of the thus obtained compound to afford 2.41 g (yield: 71%) of the captioned Compound 27 as a white crystal. Melting point: >295° C. (recrystallized from ethanol/water) Elementary analysis: $C_{16}H_{20}N_4O_2$ Calculated (%): C 63.98, H 6.71, N 18.65

Found (%): C 63.97, H 6.78, N 18.89 IR (KBr) vmax (cm$^{-1}$): 1719, 1656, 1649, 1503. NMR (CDCl$_3$, 90 MHz) δ (ppm): 11.93 (brs, 1H), 3.62 (s, 3H), 3.46 (s, 3H), 2.79 (t, 1H), 2.52–1.60 (m, 12H).

EXAMPLE 23

8-(Noradamantan-3-yl)-1,3-diethylxanthine (Compound 28)

The substantially same operations as in Example 10 were repeated using 2.0 g (10.1 mmol) of 1,3-diethyl-5,6-diaminouracil [J. Am. Chem. Soc., 75,114 (1953)] to afford 2.01 g (yield: 58%) of 6-amino-5-(noradamantane-3-carbonylamino)-1,3-diethyluracil as a light yellow powder.

NMR (CDCl$_3$, 90 MHz) δ (ppm): 7.35 (brs, 1H), 5.61 (brs, 2H), 4.18–3.85 (m, 4H), 2.76 (t, 1H), 2.50–1.10 (m, 18H).

The substantially same cyclization reaction as in Example 1 was performed except for using 1.90 g (5.49 mmol) of the thus obtained compound to afford 1.58 g (yield: 88%) of the captioned Compound 28 as a white crystal.

Melting point: 259.8°–263.1° C. (recrystallized from ethanol/water) Elementary analysis: $C_{18}H_{24}N_4O_2$ Calculated (%): C 65.83, H 7.36, N 17.05 Found (%) C 65.99, H 7.51, N 17.30 IR (KBr) vmax (cm$^{-1}$): 1704, 1646, 1497. NMR (CDCl$_3$, 90 MHz) δ (ppm): 11.93 (brs, 1H), 4.40–3.98 (m, 4H), 2.83 (t, 1H), 2.60–1.60 (m, 16H), 1.50–1.18 (m, 6H).

EXAMPLE 24

8-(Noradamantan-3-yl)-1,3-dibutylxanthine (Compound 29)

The substantially same operations as in Example 10 were repeated except for using 1.70 g (6.69 mmol) of 1,3-dibutyl-5,6-diaminouracil (U.S. Pat. No. 2,607,295) to afford 2.42 g (yield: 90%) of amorphous 6-amino-5-(noradamantane-3-carbonylamino)-1,3-dibutyluracil.

NMR (CDCl$_3$, 90 MHz) δ (ppm): 7.40 (brs, 1H), 5.59 (brs, 2H), 4.05–3.76 (m, 4H), 2.76 (t, 1H), 2.50–0.80 (m, 24H).

The substantially same cyclization reaction as in Example 1 was performed using 2.08 g (5.17 mmol) of the thus obtained compound to afford 1.87 g (yield: 94%) of the captioned Compound 29 as a light yellow powder.

Melting point: 159.7°–161.0° C. (recrystallized from ethanol/water) Elementary analysis: $C_{22}H_{32}N_4O_2$ Calculated (%): C 68.71, H 8.38, N 14.57 Found (%) C 68.69, H 8.23, N 14.81 IR (KBr) vmax (cm$^{-1}$): 1704, 1651, 1498. NMR (CDCl$_3$, 90 MHz) δ (ppm): 11.67 (brs, 1H), 4.28–3.90 (m, 4H), 2.82 (t, 1H), 2.62–1.19 (m, 18H), 1.15–0.80 (m, 6H).

EXAMPLE 25

8-(Noradamantan-3-yl)-3-isobutyl-1-methylxanthine (Compound 30)

The substantially same operations as in Example 10 were repeated except for using 1.87 g (8.81 mmol) of 1-isobutyl-3-methyl-5,6-diaminouracil [Methods in Enzymology, 9,489 (1988)] to afford 2.63 g (yield: 83%) of 6-amino-5-(noradamantane-3-carbonylamino)-1-isobutyl-3-methyluracil as a white powder.

NMR (CDCl$_3$, 90 MHz) δ (ppm): 7.35 (brs, 1H), 5.56 (brs, 2H), 3.77 (d, J=7.7 Hz, 2H), 3.34 (s, 3H), 2.76 (t, 1H), 2.40–1.50 (m, 13H), 0.99 (d, J=6.6 Hz, 6H)

The substantially same cyclization reaction as in Example 1 was performed except for using 2.60 g (7.21 mmol) of the thus obtained compound to afford 1.69 g (yield: 68%) of the captioned Compound 30 as a white needle crystal.

Melting point: 266.0°–268.7° C. (recrystallized from ethanol/water) Elementary analysis: $C_{19}H_{26}N_4O_2$ Calculated (%): C 66.64, H 7.65, N 16.36 Found (%) C 66.89, H 7.44, N 16.42 IR (KBr) vmax (cm$^{-1}$): 1708, 1652, 1495. NMR (CDCl$_3$, 90 MHz) δ (ppm): 11.72 (brs, 1H), 3.98 (d, J=7.5 Hz, 2H), 3.44 (s, 3H), 2.77 (t, 1H), 2.52–1.60 (m, 13H), 0.95 (d, J=6.6 Hz, 6H).

EXAMPLE 26

8-(Noradamantan-3-yl)-1,3-dipropyl-2-thioxanthine (Compound 31)

The substantially same operations as in Example 10 were repeated except for using 3.00 g (12.4 mmol) of 5,6-diamino-1,3-dipropyl-2-thiouracil and 2.27 g (13.6 mmol) of noradamantane-3-carboxylic acid to afford 2.95 g (yield: 60%) of amorphous 6-amino-5-(noradamantane-3-carbonylamino)-1,3-dipropyl-2-thiouracil.

NMR (CDCl$_3$, 90 MHz) δ (ppm): 7.50 (brs, 1H), 5.80 (brs, 2H), 4.60–4.25 (m, 4H), 2.72 (t, 1H), 2.40–1.50 (m, 16H), 1.20–0.80 (m, 6H).

The substantially same cyclization reaction as in Example 29 was performed except for using 2.70 g (6.92 mmol) of the thus obtained compound instead of 6-amino-5-(adamantane-1-carbonylamino)-1,3-dipropyluracil to afford 765 mg (yield: 30%) of the captioned Compound 31 as a light yellow powder.

Melting point: 216.2°–216.6° C. (recrystallized from isopropanol) Elementary analysis: $C_{20}H_{28}N_4OS$ Calculated (%): C 64.48, H 7.58, N 15.04 Found (%) C 64.49, H 7.56, N 15.35 IR (KBr) vmax (cm$^{-1}$): 1690, 1494. NMR (CDCl$_3$) δ (ppm): 11.96 (brs, 1H), 4.69 (t, 2H), 4.61 (t, 2H), 2.86 (t, 1H), 2.48–2.42 (m, 2H), 2.35–2.26 (m, 2H), 2.15–1.85 (m, 12H), 1.15–0.95 (m, 6H).

EXAMPLE 27

8-(Noradamantan-3-yl)-1,3-dipropyl-6-thioxanthine (Compound 32)

The substantially same operations as in Example 21 were repeated except for using 2.00 g (5.62 mmol) of 8-noradamantan-3-yl)-1,3-dipropylxanthine (Compound 14) prepared in Example 10 to afford 2.02 g (yield: 70%) of the captioned Compound 32 as a light yellow crystal.

Melting point: 128.5°–130.4° C. (recrystallized from acetonitrile) Elementary analysis: $C_{20}H_{28}N_4OS$ Calculated (%): C 64.48, H 7.58, N 15.04 Found (%) C 64.49, H 7.66, N 15.29 IR (KBr) vmax (cm$^{-1}$): 1,682, 1,597 and 1,495 NMR (CDCl$_3$, 90 MHz) δ (ppm): 9.65 (brs, 1H), 4.43 (t, 2H), 4.06 (t, 2H), 2.69 (t, 1H), 2.53–1.60 (m, 16H), 1.10–0.85 (m, 6H).

EXAMPLE 28

8-(Noradamantan-3-yl)-1,3-dipropyl-2,6-dithioxanthine (Compound 33)

The substantially same operations as in Example 21 were repeated except for using 2.00 g (5.38 mmol) of 8-noradamantan-3-yl)-1,3-dipropyl-2-thioxanthine (Compound 31) prepared in Example 26 to afford 1.27 g (yield: 61%) of the captioned Compound 33 as a light yellow powder.

Melting point: 94.2°–96.6° C. (recrystallized from acetonitrile) Elementary analysis: $C_{20}H_{28}N_4S_2 \cdot 0.1CH_3CN \cdot 0.2H_2O$ Calculated (%): C 61.22, H 7.30, N 14.49 Found (%): C 61.18, H 7.38, N 14.57 IR (KBr) vmax (cm$^{-1}$): 1604, 1504, 1088. NMR (CDCl$_3$, 90 MHz) δ (ppm): 9.46 (brs, 1H), 5.06 (t, 2H), 4.62 (t, 2H), 2.72 (t, 1H), 2.53–1.55 (m, 16H), 1.15–0.85 (m, 6H).

EXAMPLE 29

8-(Adamantan-1-yl)-1,3-dipropylxanthine (Compound 13)

At first, 10 g (44.3 mmol) of 1,3-dipropyl-5,6-diaminouracil was dissolved in 50 ml of pyridine, and 10.6 g (53.1 mmol) of adamantane-1-carbonylchloride was added by portions thereto at 0° C. After stirring for 30 minutes at 0° C., the mixture was concentrated under reduced pressure. A saturated aqueous sodium bicarbonate was added thereto. The residue was extracted with chloroform three times. The organic layers were combined, washed with a saturated aqueous sodium chloride, and dried over anhydrous sodium sulfate. The solvent was evaporated under reduced pressure. Then pyridine was removed from the residue by means of azeotropy with toluene to afford 19.5 g (yield: 100%) of 6-amino-5-(adamantane-1-carbonylamino)-1,3-dipropyluracil.

NMR (90 MHz; CDCl$_3$) δ (ppm): 7.47 (brs, 1H), 5.60 (brs, 2H), 4.05–3.70 (m, 4H), 2.25–1.45 (m, t9H), 1.15–0.85 (m, 6H)

Then, 100 ml of phosphorus oxychloride was added to 19.5 g of the thus obtained compound and the mixture was refluxed under heating for 30 minutes. The mixture was concentrated under reduced pressure, and a saturated aqueous sodium bicarbonate was added to the residue. The residue was extracted with chloroform three times. The extract was dried over anhydrous sodium sulfate and then the solvent was evaporated under reduced pressure. The residue was subjected to silica gel column chromatography (eluent: 20% ethyl acetate/hexane) and recrystallized from isopropanol-water to afford 2.07 g (overall yield: 13%) of the captioned Compound 13 as a white needle crystal.

Melting point: 169.3°–171.0° C. Elementary analysis: $C_{21}H_{30}N_4O_2$ Calculated (%): C 68.08, H 8.16, N 15.12 Found (%) C 68.10, H 8.30, N 15.09 IR (KBr) vmax (cm$^{-1}$): 1699, 1650, 1491 NMR (CDCl$_3$) δ (ppm): 11.70 (brs, 1H), 4.15–3.95 (m, 4H), 2.15–2.05 (m, 9H), 1.85–1.50 (m, 10H), 1.05–0.85 (m, 6H)

EXAMPLE 30

8-(Adamantan-1-yl)-1,3-dipropyl-7-methylxanthine (Compound 19)

The substantially same operations as in Example 13 were repeated except for using 2.50 g (6.76 mmol) of 8-(adamantan-1-yl)-1,3-dipropylxanthine (Compound 13) prepared in Example 29 to afford 2.16 g (yield: 83%) of the captioned Compound 19 as a white crystal.

Melting point: 79.8°–80.9° C. (recrystallized from ethanol/water). Elementary analysis: $C_{22}H_{32}N_4O_2$ Calculated (%): C 68.17, H 8.38, N 14.57 Found (%) C 68.28, H 8.47, N 14.72 IR (KBr) vmax (cm$^{-1}$): 1698, 1659. NMR (DMSO-d$_6$) δ (ppm): 4.10 (s, 3H), 3.93 (t, 2H), 3.82 (t, 2H), 2.13–2.02 (m, 9H), 1.82–1.46 (m, 10H), 0.90–0.80 (m, 6H).

Pharmaceutical preparation 1

Tablet:

A tablet having the following composition was prepared according to the conventional method.

| | |
|---|---|
| Compound 3 | 20 mg |
| Lactose | 60 mg |
| Potato starch | 30 mg |
| Polyvinyl alcohol | 3 mg |
| Magnesium stearate | 1 mg |

Pharmaceutical preparation 2

Powder:

A powder having the following composition was prepared according to the conventional method.

| | |
|---|---|
| Compound 1 | 20 mg |
| Lactose | 300 mg |

Pharmaceutical preparation 3

Syrup:

A syrup having the following composition was prepared according to the conventional method.

| | |
|---|---|
| Compound 2 | 20 mg |
| Refined saccharose | 30 mg |
| Ethyl p-hydroxybenzoate | 40 mg |
| Propyl p-hydroxybenzoate | 10 mg |
| Strawberry flavor | 0.1 ml |
| Water to make the total valume | 100 ml |

Pharmaceutical preparation 4

Capsule:

Ingredients set forth below were admixed and charged into gelatin capsules in accordance with the conventional method to thereby prepare a capsule.

| Compound 3 | 20 mg |
|---|---|
| Lactose | 200 mg |
| Magnesium stearate | 5 mg |

What is claimed is:

1. Xanthine compounds represented by the following formula (I):

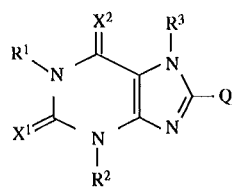

wherein $X^1$ and $X^2$ independently represent oxygen or sulfur; and Q represents:

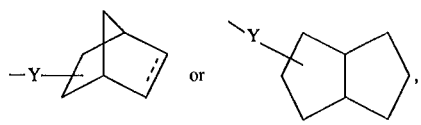

where ----- represents a single bond or a double bond; Y represents a single bond or alkylene, and $R^1$, $R^2$ and $R^3$ independently represent hydrogen or lower alkyl; or a pharmaceutically acceptable salt thereof.

2. The compound according to claim 1, wherein both of $R^1$ and $R^2$ are lower alkyl and $R^3$ is hydrogen; and both of $X^1$ and $X^2$ are oxygen.

3. The compound according to claim 2, wherein Q is

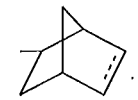

4. The compound according to claim 2, wherein Q is

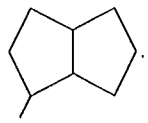

5. A pharmaceutical composition comprising a pharmaceutical carrier and, as an active ingredient, an effective amount of a xanthine compound as defined by claim 1 or a pharmaceutically acceptable salt thereof.

* * * * *

UNITED STATES PATENT AND TRADEMARK OFFICE
CERTIFICATE OF CORRECTION

PATENT NO. : 5,525,607

DATED : June 11, 1996

INVENTOR(S) : FUMIO SUZUKI ET AL.

It is certified that error appears in the above-identified patent and that said Letters Patent is hereby corrected as shown below:

ON TITLE PAGE

Item: [75] INVENTORS:
"Fumio Suzuki, Mishima; Junichi Shimada, Shizuoka-ken; Akio Ishii, Shizuoka-ken; Tetsuji Ohno, Shizuoka-ken; Akira Karasawa, Shizuoka-ken; Kazuhiro Kubo, Shizuoka-ken; Hiromi Nonaka, Shizuoka-ken; Fumio Suzuki, Mishima; Junichi Shimada, Shizuoka-ken; Akio Ishii, Shizuoka-ken; Tetsuji Ohno, Shizuoka-ken, all of Japan; Akira Karasawa, Huntingdom Valley, Pa; Kazuhiro Kubo; Hiromi Nonaka, both of Shizuoka-ken, Japan" should read
--Fumio Suzuki, Junichi Shimada, Akio Ishii, Tetsuji Ohno, Akira Karasawa, Kazuhiro Kubo, Hiromi Nonaka all of Shizuoka-ken, Japan--.

COLUMN 2

Line 37, "propyplene," should read --propylene,--.

COLUMN 6

Line 3, "reaction:" should read --reaction--.

UNITED STATES PATENT AND TRADEMARK OFFICE
CERTIFICATE OF CORRECTION

PATENT NO. : 5,525,607
DATED : June 11, 1996
INVENTOR(S) : FUMIO SUZUKI ET AL.

Page 2 of 3

It is certified that error appears in the above-identified patent and that said Letters Patent is hereby corrected as shown below:

COLUMN 15

Line 9, "Precipitate" shoudl read --precipitate--.

COLUMN 20

Line 14, "be" shoudl read --is--.
Line 40, "are" should read --are the--.

COLUMN 22

Line 3, "[2.2.1)" should read --[2.2.1]--.

COLUMN 23

Line 52, "Jx6.8," should read --J=6.8,--.

COLUMN 25

Line 33, "1,704,." should read --1,704,--.
Line 63, "-2bicyclo" should read --2-bicyclo--.

COLUMN 26

Line 1, "stirring" should read --stirred--.
Line 29, "8-8(1R*," should read --8-[(IR*,--.

COLUMN 30

Line 21, "9,489" should read --159,489--.

UNITED STATES PATENT AND TRADEMARK OFFICE
CERTIFICATE OF CORRECTION

PATENT NO. : 5,525,607
DATED : June 11, 1996
INVENTOR(S) : FUMIO SUZUKI ET AL.

It is certified that error appears in the above-identified patent and that said Letters Patent is hereby corrected as shown below:

<u>COLUMN 31</u>

Line 56, "(m, t9H)," should read --(m, 19H),--.

Signed and Sealed this

Twenty-eighth Day of January, 1997

Attest:

BRUCE LEHMAN

Attesting Officer    Commissioner of Patents and Trademarks